US006504065B1

(12) United States Patent
Enlow et al.

(10) Patent No.: US 6,504,065 B1
(45) Date of Patent: Jan. 7, 2003

(54) METHOD OF MAKING METAL SALTS OF 2,4,6-TRI-T-BUTYLPHENOL

(75) Inventors: William Palmer Enlow, Belpre, OH (US); Gary Vincent Marlin, Morgantown, WV (US)

(73) Assignee: General Electric Company, Pittsfield, MA (US)

( * ) Notice: Subject to any disclaimer, the term of this patent is extended or adjusted under 35 U.S.C. 154(b) by 0 days.

(21) Appl. No.: 09/676,845

(22) Filed: Sep. 29, 2000

(51) Int. Cl.$^7$ ............................................... C07C 39/06
(52) U.S. Cl. ........................ 568/784; 568/780; 568/781
(58) Field of Search ................................ 568/781, 784, 568/780

(56) References Cited

U.S. PATENT DOCUMENTS

| 3,281,506 A | | 10/1966 | Shepard et al. |
| 3,418,348 A | * | 12/1968 | Shepard |
| 3,839,506 A | | 10/1974 | Hechenbleikner et al. |
| 3,888,903 A | * | 6/1975 | Chupp |
| 3,994,838 A | * | 11/1976 | Thompson |
| 4,116,926 A | | 9/1978 | York |
| 4,237,075 A | | 12/1980 | Gough |
| 4,290,976 A | | 9/1981 | Hechenbleikner et al. |
| 4,312,818 A | | 1/1982 | Maul et al. |
| 4,371,647 A | | 2/1983 | Minagawa et al. |
| 4,440,696 A | | 4/1984 | Maul et al. |
| 4,492,661 A | | 1/1985 | Maul et al. |
| 4,656,302 A | | 4/1987 | Dressler |
| 4,705,879 A | | 11/1987 | Dressler |
| 4,739,090 A | | 4/1988 | Tajima et al. |
| 4,894,481 A | | 1/1990 | Burt |
| 5,126,475 A | | 6/1992 | Bahrmann et al. |
| 5,141,975 A | | 8/1992 | Enlow |
| 5,294,597 A | * | 3/1994 | Foster |
| 5,438,086 A | | 8/1995 | Stevenson et al. |

OTHER PUBLICATIONS

Houben–Weyl: "Methoden der organischen Chemie, Band VI/1c, Phenole, Teil 2" 1976, Georg Thieme Verlag, Stuttgart, XP002189867 * p. 1189, second complete paragraph *.

* cited by examiner

*Primary Examiner*—Michael L. Shippen

(57) ABSTRACT

Reaction of a phenol with a metal salt of an alcohol produces a metal phenolate salt of a phenol. When a hindered phenol is used a hindered metal phenolate is produced. Such hindered metal phenolate salts are useful in driving the synthesis reaction of hindered phenol esters and phosphite esters to completion.

9 Claims, No Drawings

METHOD OF MAKING METAL SALTS OF 2, 4,6-TRI-T-BUTYLPHENOL

FIELD OF THE INVENTION

The present invention is directed to a method of making metal salts of phenols. More particularly the present invention is directed to a method of making metal salts of hindered phenols.

BACKGROUND OF THE INVENTION

Organic phosphites are used in the stabilization of a wide variety of polymeric systems. Many different phosphites have been proposed for use either alone or in combination with other stabilizers. Such phosphites and their utilities are described in U.S. Pat. Nos. 4,371,647, 4,656,302, 4,705,879, 5,126,475, 5,141,975, and 5,438,086. The importance of organic phosphites as stabilizers has lead to the development of a variety of specialty organic phosphites that have enhanced effectiveness for stabilization.

Sterically hindered organic phosphites, and in particular phosphites based upon glycols or polyhydric alcohols (e.g. pentaerythritol) and containing alkyl, aryl, or alkyl-substituted aryl groups wherein the substitution is selected from the group consisting of t-butyl, t-amyl, t-hexyl, cyclohexyl, t-pentyl, and t-octyl, are especially desirable compounds due to their enhanced hydrolytic stability, ease of handling and compatibility with a wide variety of polymeric systems. The phosphite esters prepared from sterically hindered alcohols are also especially preferred for their improved hydrolytic stability over other alkyl substituted phosphites as well as their enhanced compatibility with some polymeric resins, especially polyolefins.

The organic diphosphites are generally prepared using methods involving reactions between the appropriate hydroxy compounds and phosphorous trihalides, e.g., phosphorous trichloride. Such methods and other useful methods are described in U.S. Pat. Nos. 3,839,506, 4,116,926, 4,290,976, 4,440,696, and 4,492,661. The ease of substitution of the halides on the phosphorous trihalide decreases as each halide is replaced. For example, in the preparation of bis(aryl)pentaerithritol diphosphites, the pentaerithritol hydroxyls readily react with a phosphorous trihalide to yield a bis(disubstituted halo phosphite (i.e., an intermediate di-substituted diphosphorohalidite). The displacement of the third halo group is less than quantitative and is considerably slower in rate. Additionally, displacement of the third halo group by a sterically hindered phenol is even more difficult and requires elevated temperatures and/or use of a catalyst.

In order to increase the rate of reaction and the degree of completion for displacing the third halide with a sterically hindered moiety, various techniques have been generally utilized in the art. These techniques include: elevating the reaction mixture temperature and the use of hydrogen halide acceptors, e.g., amines. Such techniques are described in U.S. Pat. Nos. 3,281,506, 4,237,075, 4,312,818, 4,440,696, and 4,894,481.

Generally in the case of diphosphites derived from sterically hinderd alcohols, the procedures of the prior art result in undesirable product mixtures. Additionally, various by-product phosphite compounds are also formed leading to low yields of the desired product. The resulting phosphite mixture containing a halo-phosphite is extremely difficult to purify and the residual halo-phosphite can lead to acid impurities that affect the long term stability of the desired organic phosphite, as wellas affecting the stability of thermoplastic compositoins where the phosphite is employed as a stabilizer.

Various processes have been described in the prior art yet each suffers from some undesirable limitation. For example, U.S. Pat. No. 4,739,090 describes a process utilizing xylene as a solvent. The final product is isolated by filtration and the filtrate can be recycled. This process is deficient in resulting in at least about five percent or more impurities that require further crystallization to remove. This patent is silent on the form of the pentaerythritol utilized in the reaction.

U.S. Pat. No. 5,103,035 describes low temperature reaction conditions in chlorinated solvents. This process is undesirable due the difficulties in safely handling chlorinated solvents and a second solvent has to be utilized in order to bring the final product out of solution.

U.S. Pat. No. 5,438,086 describes a process for making diphosphites based upon pentaerythritol and 2,4-dicumylphenol wherein the dicumyl phenol is first reacted with phosphorous trichloride followed by allowing the reaction with the pentaerythritol. This process afforded only a 66% yield and acid numbers of 2 to 6, both of which are unacceptable.

The process of making metal salts of hindered phenols has generally required an ammonia solution of an alkali metal to be reacted with the hindered phenol in order to yield the metal phenbolate salt (Houben-Weyl, Methoden der Organischen Chemie, Phenolen, vol. VI/1c, p. 1189 (1976)).

It is therefore apparent that a need continues to exist for improved processes for the preparation of phosphite esters prepared from sterically hindered alcohols and phenols.

SUMMARY OF THE INVENTION

The process of the present invention provides for a process for the preparation of a metal phenolate comprising reacting a phenol having the formula:

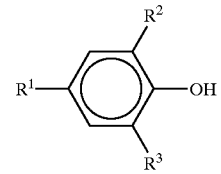

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl with a metal alcoholate having the formula $(R^4O)_xQ$ where $R^4O$ is derived from the corresponding alcohol $R^4OH$, Q is a metal cation having a valence x, to produce a metal phenolate and an alcohol $R^4OH$ wherein said metal phenolate has the formula:

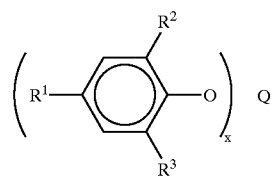

wherein Q,x and each $R^1$, $R^2$, and $R^3$ are as previously defined and removing the alcohol $R^4OH$ from the metal phenolate. The present invention further provides for conducting the process of the invention in the presence of a solvent.

DETAILED DESCRIPTION OF THE INVENTION

The present invention comprises a process to convert phenols, abbreviated ΦOH, of the formula

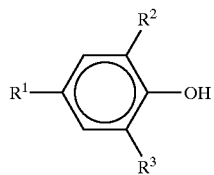

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl to a metal phenolate, abbreviated $(\Phi O)_x Q$, of the formula:

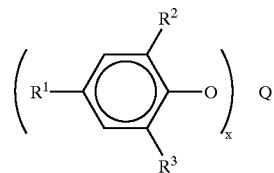

where each $R^1$, $R^2$, and $R^3$ is selected from the group consisting of hydrogen, methyl, ethyl, n-propyl, iso-propyl, n-butyl, t-butyl, t-amyl, t-hexyl, cyclohexyl, cumyl, t-pentyl, and t-octyl, and Q is a metal cation having a valence x, i.e oxidation state. It should be noted that the choices for $R^1$, $R^2$, and $R^3$ of the phenol become the choices for $R^1$, $R^2$, and $R^3$ of the metal phenolate. Further when $R^1$, $R^2$, and $R^3$ are selected from the group consisting of n-propyl, iso-propyl, n-butyl, t-butyl, t-amyl, t-hexyl, cyclohexyl, cumyl, t-pentyl, and t-octyl the phenol is considered a hindered phenol. The oxidation state or valence (used interchangeably herein) of the metal cation Q may vary in integer values between 1 and 4. Q may be any metal cation that is synthetically convenient, wherein the corresponding phenolate salt may correspond to the phenolate esters used for the preparation of the phosphite esters of hindered alcohols. The metal cations, Q, most suitable for the metal phenolate salt are selected from the group consisting of the alkali metals, the alkaline earth metals, the transition metals and the non-transition metals of Groups III, IV and V subject to the limitation that the halides of these metals are ionic salts. By halides the term includes the elements of Group VII of the periodic table, i.e. fluorine, chlorine, bromine, iodine and astatine. Preferred metals are the alkali metals and the alkaline earth metals; more preferred metals are the alkali metals; and the most preferred metals are sodium and potassium.

The present invention comprises the following process: (a) reacting $\Phi OH$, preferably a hindered phenol, with $(R^4O)_x Q$, a metal alcoholate, in a reaction mixture to produce reaction products comprising $R^4OH$ and $(\Phi O)_x Q$, where x is as previously defined and (b) removing $R^4OH$ from the reaction products. $R^4OH$ is any alcohol where R4 is any monovalent organic radical, preferably $R^4$ may be a 1 to 20 carbon atom organic monovalent radical. More preferably $R^4$ is selected from the group of monovalent organic radicals consisting of methyl, ethyl, n-propyl, iso-propyl, n-butyl, 2-butyl, 2-methyl-propyl and tertiary butyl. The process of the present invention may be conducted in any chemically convenient fashion known in the art, particularly in solution. A particularly convenient method of preparation involves the use of an amine solvent for the phenol precursor, $\Phi OH$, dissolving or in the case where the metal alcoholate is not soluble in the solvent slurrying a metal alcoholate, $(R^4O)_x Q$, therein, reacting the phenol precursor and the metal alcoholate to produce the metal phenolate, $(\Phi O)_x Q$, and $R^4OH$ and removing the $R^4OH$.

The $R^4OH$, or product alcohol, may be removed in any number of means known in the art, for example by distillation of the alcohol away from the reaction products, by distillation under vaccuum with or without the application of heat, by liquid liquid extraction, either concurrent or countercurrent, or by treatment with another solvent to induce a phase separation that also separates the two reaction products $R^4OH$ and $(\Phi O)_x Q$ from each other. These various techniques of removing the product alcohol, $R^4OH$, may be amplified in their efficacy by the application of a temperature differential, i.e. either by selectively heating or cooling to increase the amount of the $R^4OH$ removed from the reaction products.

When it is desired to perform the process of the present invention in solution an aprotic organic solvent should be used. Depending on solubility concerns the aprotic solvent may be either non-polar or dipolar. Examples of aprotic organic solvents include aliphatic hydrocarbons e.g. pentane, hexane, heptane, octane and the like, iso-pentane, iso-hexane, iso-heptane, iso-octane and the like, aromatic hydrocarbons, e.g. benzene, toluene, and xylene, mesitylene, naphthalene and the like, halogentated aliphatic hydrocarbons, e.g. methylene chloride, chloroform, carbon tetrachloride, dichloromethane, 1,2-dichloro-ethane; halogenated aromatic hydrocarbons such as chlorobenzene and dichlorobenzene; esters such as ethyl acetate, butyl acetate and ethyl benzoate; ketones e.g. acetone, methyl ethyl ketone and the like; ethers such as diethylether, di-isopropylether, t-butyl methyl ether, dimethoxyethane, dioxane, tetrahydrofuran, glycolethers, such as ethyleneglycol-methylether, ethyleneglycol-ethylether, diethyleneglycol-monomethylether or diethyleneglycol-monoethylether and the like; nitrogen compounds such as alkyl amines such as tri-methyl amine, tri-ethyl amine tri-propyl amine, tri-propyl amine, tri-iso-propyl amine and the like, acetonitrile, dimethylacetamide, benzonitrile, N,N-dimethylformamide, N,N-dimethylacetoamide, nitrobenzene, N-methylpyrrolidone, aromatic N-heterocycles, such as pyridine, picoline or quinoline; sulfur compounds such as carbon disulfide and dimethyl sulfoxide; phosphorus compounds such as hexamethylphosphoramide; and combinations thereof.

The present invention describes the reaction of a phenol with a metal salt of an alcohol, i.e. a metal alcoholate, to produce a metal phenolate salt of a phenol. Preferably the process of the present invention utilizes a hindered phenol. Such salts are particularly useful in driving the synthesis reaction of hindered phenol esters (e.g. reactions with acyl halides) and phosphite esters (e.g reactions with halo-phosphites or halo-phosphates) to completion.

EXPERIMENTAL 66.9 g of 2,4,6-tri-t-butylphenol was dissolved or dispersed into 213.5 g of tri-n-propyl amin. To this solution was added 13.5 of sodium methoxide. The mixture was heated in flask until reflux occurred at about 150° C. When the reflux temperature dropped below 150° C., distillate was condensed and removed from the reaction mixture until the vapor temperature in the flask rose above 150° C. then the mixture was again refluxed. When the vapor temperature dropped below 150° C., distillate was condensed and removed from the reaction mixture until the vapor temperature rose above 150° C. This alternate process of reflux and condensation was repeated until 8.0 g of methyl alcohol, $CH_3OH$ had been distilled Away from the reaction mixture. Approximately 112 g of tri-n-propyl amine was stripped from the reaction mixture leaving about 71 g of sodium 2,4,6-tri-t-butyl phenolate in about 100 g of tri-n-propyl amine as a 40 weight percent slurry of the phenolate salt in the amine solvent.

Having described the invention, that which is claimed is:

1. A process for the preparation of a metal phenolate for making a hindered phosphite ester, comprising:

forming a reaction mixture comprising:
      a phenol having the formula:

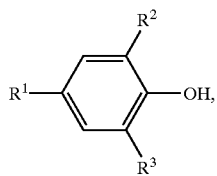

wherein each $R^1$, $R^2$, and $R^3$ is independently selected from the group consisting of methyl, ethyl, n-propyl, iso-propyl, n-butyl, t-butyl, t-amyl, t-hexyl, cyclohexyl, cumyl, t-pentyl, and t-octyl;

an amine solvent, and a metal alcoholate having the formula $(R^4O)_xQ$, wherein $R^4O$ is derived from the corresponding alcohol $R^4OH$; and Q is a metal cation having a valency x;

heating the reaction mixture; and removing the alcohol $R^4OH$ from the reaction mixture, wherein $R^4$ is as previously defined;

wherein said metal phenolate has the formula:

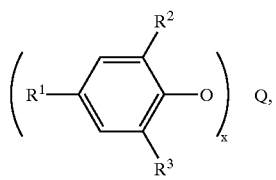

wherein Q, x, and each $R^1$, $R^2$, and $R^3$ are as previously defined.

2. The process of claim 1 wherein $R^4$ is a monovalent organic radical having from one to twenty carbon atoms.

3. The process of claim 1 wherein $R^4$ is selected from the group consisting of methyl, ethanyl, n-propyl, iso-propyl, n-butyl, 2-butyl, 2-methyl-propyl and tertiary butyl.

4. The process of claim 1, where Q is a metal cation comprising ionic salts of the alkali metals, the alkaline earth metals, and Groups III, IV, and V transition metals and non-transition metals.

5. The process of claim 1, wherein the amine solvent is selected from the group consisting of trimethylamine, triethylamine, tri-n-propylamine, tri-iso-propylamine, pyridine, picoline, and quinoline.

6. A process for the preparation of an alkali metal 2,4,6-tri-tert-butylphenolate for making a hindered phosphite ester, comprising:

forming a reaction mixture comprising:
      2,4,6-tri-tert-butylphenol, an amine solvent,
      an alkali metal alcoholate having the formula $(R^4O)Q'$, wherein $R^4O$ is derived from the corresponding alcohol $R^4OH$; and $Q'$ is an alkali metal cation, and
      an amine solvent;
   heating the reaction mixture; and
   removing the alcohol $R^4OH$ from the reaction mixture.

7. The process of claim 6, wherein the alkali metal is sodium.

8. The process of claim 6, wherein $R^4$ is methyl.

9. The process of claim 6, wherein the amine solvent is selected from the group consisting of trimethylamine, triethylamine, tri-n-propylamine, tri-iso-propylamine, pyridine, picoline, and quinoline.

* * * * *